United States Patent
Nowak et al.

(10) Patent No.: US 6,734,315 B1
(45) Date of Patent: May 11, 2004

(54) THIN-FILM EPOXIDATION OF AN UNSATURATED OIL OR ALKYL FATTY ACID ESTER

(75) Inventors: James A. Nowak, Naperville, IL (US); Thomas A. Zillner, Lake Bluff, IL (US); Leslie Patrick Mullin, III, Elmhurst, IL (US)

(73) Assignee: The C.P. Hall Company, Chicago, IL (US)

( * ) Notice: Subject to any disclaimer, the term of this patent is extended or adjusted under 35 U.S.C. 154(b) by 0 days.

(21) Appl. No.: 10/607,616

(22) Filed: Jun. 27, 2003

(51) Int. Cl.⁷ ................. C07D 301/18; C07D 301/14

(52) U.S. Cl. ................. 549/527; 549/528; 549/523

(58) Field of Search ................. 549/523, 527, 549/528

(56) References Cited

U.S. PATENT DOCUMENTS

| | | | | | |
|---|---|---|---|---|---|
| 3,207,743 | A | * | 9/1965 | Bried | 530/232 |
| 3,778,465 | A | * | 12/1973 | Barnstorf | 554/143 |
| 4,215,058 | A | * | 7/1980 | Jourdan-Laforte | 549/527 |

* cited by examiner

*Primary Examiner*—Amelia A. Owens
(74) *Attorney, Agent, or Firm*—Marshall, Gerstein & Borun LLP (57) ABSTRACT

A method of epoxidizing an unsaturated compound having a carbon-to-carbon double bond to form an oxirane ring across the double bond comprising adding to said unsaturated compound an oxidizing agent selected from hydrogen peroxide, acetaldehyde monoperacetate, an organic hydroperoxide, or a combination thereof, to form a reactant mixture; and forming the reactant mixture in a film against a wall of the thin-film reactor that is at a temperature sufficient for reaction of the oxidizing agent with the unsaturated compound to form an oxirane ring across a double bond of the unsaturated compound.

12 Claims, 4 Drawing Sheets

FIG. 1A
PRE-FORMED PERACID EPOXIDATION

PRIOR ART

FIG. 1B

IN-SITU EPOXIDATION

PRIOR ART

THIN-FILM EPOXIDATION OF AN UNSATURATED OIL OR ALKYL FATTY ACID ESTER

FIELD OF THE INVENTION

The present invention is directed to a method and apparatus for epoxidizing an unsaturated oil or an alkyl fatty acid ester, particularly an unsaturated vegetable oil, such as soybean oil, linseed oil, or an ester of tall oil fatty acids. More particularly, the invention is directed to a thin-film method of epoxidizing an oil or an alkyl fatty acid ester by combining the oil or alkyl fatty acid ester with an oxidizing agent, such as hydrogen peroxide, for reaction (epoxidation) with the oil or alkyl fatty acid ester, in a thin-film reactor.

BACKGROUND

Epoxy plasticizers, such as epoxidized unsaturated oils and, epoxidized alkyl fatty acid esters, particularly epoxidized soybean oil and epoxidized octyl esters of tall oil fatty acids can be manufactured by oxidation of either olefinic or aromatic double bonds, as follows:

Hydrogen peroxide and the unsaturated oil or the alkyl fatty acid-ester alone do not react to any significant extent in prior art processes, and an organic peracid (usually acetic acid or formic acid) is necessary to shuttle the active oxygen from the aqueous phase to the oil phase. Once in the oil phase, the peracid adds oxygen across the carbon-to-carbon double bond and regenerates the original acid. On a commercial scale, epoxidation of soybean oil is achieved by oxidation of soybean oil with peracetic acid where the peracetic acid is derived from the oxidation of acetic acid with hydrogen peroxide, in-situ, in the presence of the soybean oil. In one process, peracetic acid generated in a process for oxidation of acetaldehyde to acetic acid has been isolated and used in the epoxidation process. This preformed peracetic acid can be handled, with proper precautions, in an inert solvent such as ethyl acetate or acetone. Others have found that an intermediate in the acetaldehyde oxidation process, acetaldehyde monoperacetate, also can be used as an epoxidizing agent. While oxidation of olefins by hydroperoxides is described in the literature, these prior art processes are far less efficient than the peracid processes.

Figure 1A:
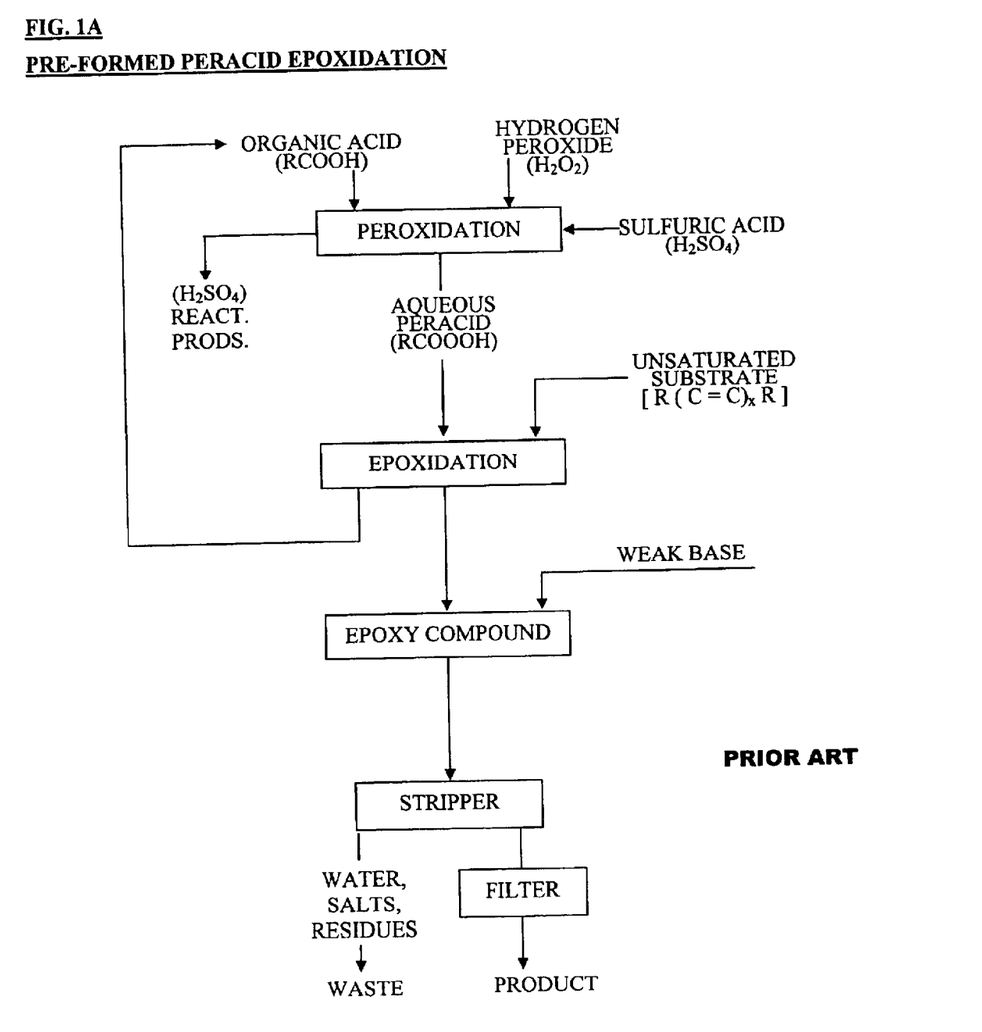
FIGS. 1A and 1B are schematic flow diagrams of prior art preformed and in-situ peracid process for epoxidizing an unsaturated substrate, such as soybean oil or an alkyl fatty acid ester.
Figure 1B:
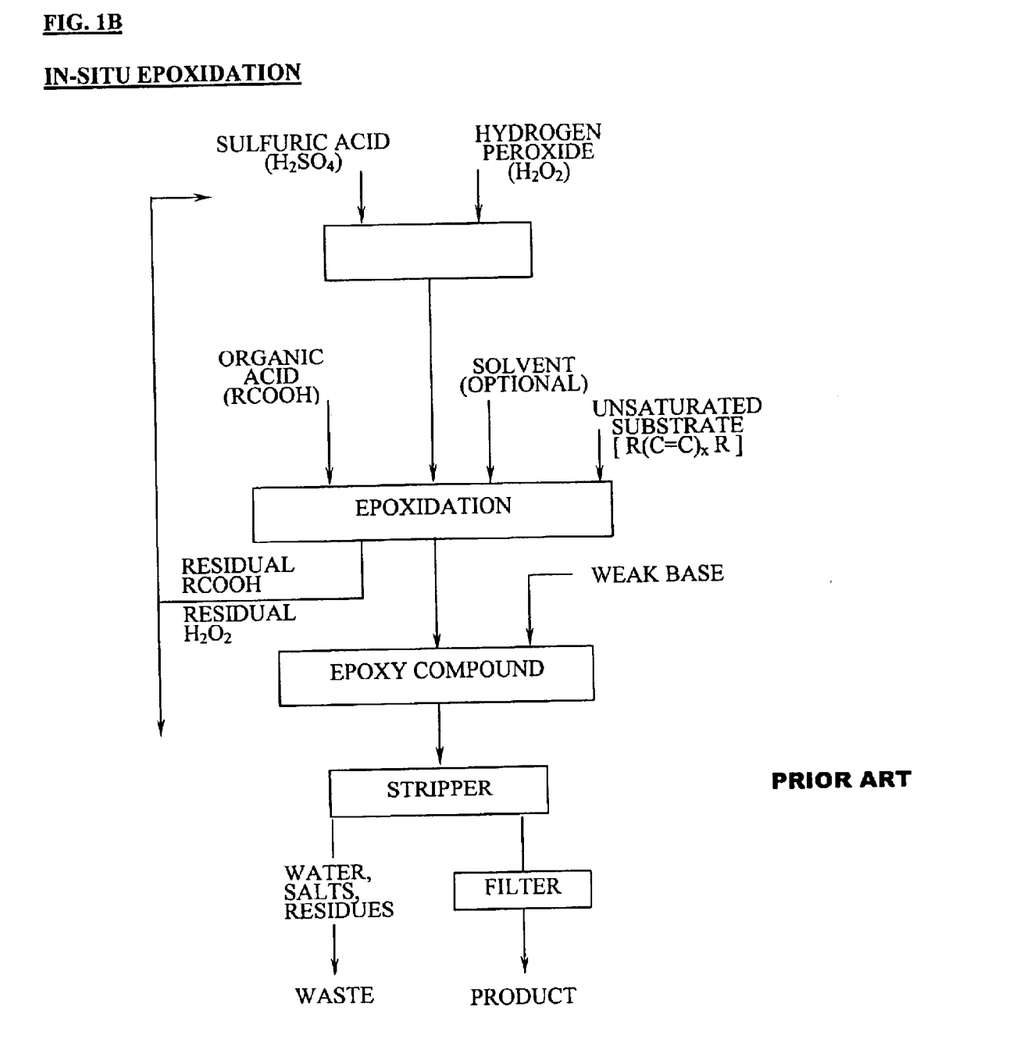

The epoxidation processes can be divided into two basic types. In the first, the peracid is preformed; in the second, the peracid is formed in-situ in the primary reaction vessel. Representative schematics for the preformed and in-situ processes are shown in FIGS. 1A and 1B, respectively. The processes claimed herein are directed to a new and improved thin-film reaction process capable of efficiently reacting hydrogen peroxide directly with an unsaturated vegetable oil or alkyl fatty acid ester without first forming a peracid reactant.

PREFORMED PERACETIC EPOXIDATION

The use of preformed peracetic acid results in epoxidation without catalyst at temperatures of 20 to 60° C. at atmospheric pressure, as follows:

The peroxidation of acetic acid with hydrogen peroxide is not efficient except at high molar ratios of acetic acid to hydrogen peroxide, resulting in large amounts of acetic acid to be recovered. In addition, concentrations of peracetic acid above 40 to 45 wt. % in acetic acid are explosive at epoxidation temperatures. Such processes require large volume production on an essentially continuous basis since the preformed peracid cannot be safely stored.

IN-SITU EPOXIDATION—ACID CATALYZED

Experience has shown that the in-situ process is safer than processes using preformed peracids. In general, a peroxide solution (35% to 70% $H_2O_2$ in water) containing small quantities of a strong mineral acid catalyst, such as sulfuric acid or phosphoric acid, or styrene sulfonic acids, is added to a mixture of an epoxidizable substrate and acetic acid or formic acid at atmospheric pressure. As the reactants mix, the hydrogen peroxide and the acetic or formic acid react in the presence of the mineral acid catalyst to form the peracid, as follows:

To prevent uncontrolled exotherm and to optimize epoxidation, the peroxide solution is added in several increments with agitation, and the reaction temperature is maintained at 50° C. to 65° C. for periods of 10 to 40 minutes per incremental addition of peroxide. One of the biggest problems with this process is that only small batch quantities of peracid can be formed in the presence of the unsaturated substrate. The peracid reacts with the unsaturated portion of the molecule and is quickly depleted, preventing a build-up of detonatable quantities of peroxide compounds, as follows:

Further, significant problems are encountered in separation of the epoxidized substrate from the water, acid and peroxide remaining with the product after reaction. When the iodine number of the substrate has been reduced to the desired level, e.g., 0.5 to 10, the reaction is stopped and the epoxidized substrate is then difficult to separate from the aqueous layer since the aqueous layer contains a mixture of water, organic acid and some peroxide. Further, the epoxy layer contains acid catalyst that must be neutralized by a mild base, and residual peroxide that must be decomposed.

The epoxy then is washed, centrifuged, decanted, filtered and transferred to a stripper where water and non-product residues are removed.

Most, if not all of the above-identified difficulties of the known epoxidation processes are eliminated, or substantially reduced in accordance with the processes described herein.

SUMMARY

The processes described herein take advantage of thin-film reactor apparatus for epoxidizing an unsaturated substrate, particularly an unsaturated oil, such as soybean oil, linseed oil, or an alkyl ester of a fatty acid (hereinafter, the epoxidized unsaturated oil and/or the epoxidized alkyl fatty acid ester are referred to as the "epoxidized substrate") by directly reacting the unsaturated substrate with an oxidizing agent, such as hydrogen peroxide, acetaldehyde monoperacetate, an organic hydroperoxide, or a mixture thereof. The process can be operated continuously while continuously stripping most of the water from the epoxidized product in the thin-film reactor. Theoretically, the thin-film reactor processes described herein can strip sufficient water from the reaction product (epoxidized substrate) so that the epoxidized substrate requires little or no additional purification.

Accordingly, one aspect of the processes described herein is the rapid removal of water, in the vapor phase, to allow increased rates of reaction (epoxidation) of unsaturated compounds.

Another aspect of the processes is the elimination or substantial reduction of the neutralization, centrifuging, washing, decanting, and/or filtration steps needed with the presently practiced epoxidation processes.

BRIEF DESCRIPTION OF THE DRAWINGS

The above and other aspects and advantages of the methods and apparatus described herein are better understood with reference to the drawings and the following detailed description of the preferred embodiments, wherein.

DETAILED DESCRIPTION OF THE PREFERRED EMBODIMENTS

The thin-film processes described herein are useful for epoxidation of any unsaturated organic compound having at least one carbon-to-carbon double bond. The processes are particularly useful in the manufacture of epoxidized ester plasticizers, such as epoxidized alkyl fatty acid esters and epoxidized vegetable oils, particularly epoxidized soybean oil.

Throughout this specification, ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

The preferred alkyl fatty acid esters may be unsaturated compounds that can be epoxidized in accordance with the methods and apparatus described herein are the vegetable oils, particularly, soybean oil and linseed oil. The following vegetable oils (Table 1) can be epoxidized in accordance with the methods and apparatus described herein to yield commercially acceptable products.

TABLE 1

Vegetable Oil Substrates For Epoxy Plasticizers

| Vegetable Oil | Iodine Number[1] | Number of Double Bonds Per 100 gms. | Theoretical Oxirane Oxygen, % |
|---|---|---|---|
| Linseed | 170–204 | 0.670–0.800 | 9.67–11.9 |
| Safflower | 141–150 | 0.552–0.591 | 8.11–8.63 |
| Soybean | 120–141 | 0.474–0.556 | 7.03–8.16 |
| Corn | 102–128 | 0.406–0.504 | 6.09–7.44 |
| Cottonseed | 99–113 | 0.390–0.445 | 5.87–6.65 |
| Rapeseed | 97–108 | 0.382–0.426 | 5.76–6.37 |
| Peanut | 84–100 | 0.331–0.394 | 5.03–5.93 |

[1]gms of $I_2$/100 gms of oil.

In addition to the unsaturated oils described above, another preferred class of esters which can be epoxidized in accordance with the methods and apparatus and apparatus described herein are monoesters, diesters, triesters, or mixtures thereof, that have radicals $R^1$ and $R^2$, straight chain or branched, wherein at least one of the radicals $R^1$ and/or $R^2$ have one, two or three double bonds in the hydrocarbon chain.

The preferred monoesters have a formula I, as follows:

(I)

wherein $R^1$ is a $C_3$–$C_{24}$ alkyl, preferably $C_3$–$C_{18}$ alkyl, more preferably $C_6$–$C_{18}$ alkyl, straight chain or branched, containing 1 to 3 carbon-to-carbon double bonds. $R^2$ is a $C_3$–$C_{24}$, preferably $C_6$–$C_{24}$, more preferably $C_8$–$C_{18}$ saturated hydrocarbon, or an unsaturated hydrocarbon having 1 to 6, preferably 1 to 3 carbon-to-carbon double bonds.

The preferred diesters have a formula II or III, as follows:

(II)

wherein n=3–24, preferably 6–18, and more preferably 3–10, and $R^3$ and $R^4$, same or different, are $C_3$–$C_{24}$ alkyl, preferably $C_3$–$C_{18}$ alkyl, more preferably $C_6$–$C_{18}$ alkyl radicals, straight chain or branched, containing 1 to 3 carbon-to-carbon double bonds, with at least one of the radicals $R^3$ and/or $R^4$ containing at least one carbon-to-carbon double bond.

(III)

wherein $R^5$ and $R^7$, same or different, are $C_3$–$C_{24}$ alkyl, preferably $C_6$–$C_{24}$ alkyl, more preferably $C_8$–$C_{18}$ alkyl, straight chain or branched, either saturated or containing 1 to 6, preferably 1 to 3, carbon-to-carbon double bonds;

$R^6$ and $R^8$, same or different, are $C_3$–$C_{24}$ alkyl, preferably $C_3$–$C_{18}$ alkyl, more preferably $C_6$–$C_{18}$ alkyl, straight chain or branched, saturated or unsaturated containing 1 to 3 carbon-to-carbon double bonds; and $R^{10}$ and $R^{11}$, same or different, are $C_3$–$C_{24}$ saturated hydrocarbon chains, preferably $C_3$–$C_{18}$, more preferably $C_6$–$C_{18}$, straight chain or branched; or unsaturated $C_3$–$C_{24}$ hydrocarbon chains, preferably $C_3$–$C_{18}$, more preferably $C_6$–$C_{18}$, straight chain or branched, containing 1 to 6, preferably 1 to 3, carbon-to-carbon double bonds. At least one of the radicals $R^6$, $R^8$, $R^{10}$ and/or $R^{11}$ of formula III should contain at least one carbon-to-carbon double bond.

The preferred triesters have a formula IV, as follows:

(IV)

wherein $R^{12}$, $R^{14}$ and $R^{18}$, same or different, are $C_3$–$C_{24}$ alkyl, preferably $C_6$–$C_{24}$ alkyl, more preferably $C_8$–$C_{18}$ alkyl, straight chain or branched, either saturated or containing 1 to 6, preferably 1 to 3, carbon-to-carbon double bonds;

$R^{13}$, $R^{15}$ and $R^{19}$, same or different, are $C_3$–$C_{24}$ alkyl, preferably $C_3$–$C_{18}$ alkyl, preferably $C_6$–$C_{18}$ alkyl, straight chain or branched, saturated or unsaturated containing 1 to 3 carbon-to-carbon double bonds; and

$R^{16}$, $R^{17}$ and $R^{20}$, same or different, are $C_3$–$C_{24}$ saturated hydrocarbon chains, preferably $C_3$–$C_{18}$, more preferably $C_6$–$C_{18}$, straight chain or branched; or unsaturated $C_3$–$C_{24}$ hydrocarbon chains, preferably $C_3$–$C_{18}$, more preferably $C_6$–$C_{18}$, straight chain or branched, containing 1 to 6, preferably 1 to 3, carbon-to-carbon double bonds. At least one of the radicals $R^{13}$, $R^{15}$, $R^{16}$, $R^{17}$, $R^{19}$ and/or $R^{20}$ should contain at least one carbon-to-carbon double bond.

The fatty acid residues or hydrocarbon chains $R^2$, $R^5$, $R^7$, $R^{12}$, $R^{14}$ and $R^{18}$ of the esters of formulas I, II, III, and IV can be any $C_3$–$C_{24}$, preferably $C_6$–$C_{24}$, more preferably $C_8$–$C_{18}$, hydrocarbon chain, either saturated or containing 1 to 6, preferably 1 to 3, carbon-to-carbon double bonds, derived from animal or vegetable fatty acids such as butter; lard; tallow; grease; herring; menhaden; pilchard; sardine; babassu; castor; coconut; corn; cottonseed; jojoba; linseed; oiticica; olive; palm; palm kernel; peanut; rapeseed; safflower; soya; sunflower; tall; and/or tung. Examples are the hydrocarbon chain residues from the following fatty acids, where the number in parentheses indicates the number of carbon atoms, and the number of double bonds, e.g., $(C_{24\text{-}6})$ indicates a hydrocarbon chain having 24 carbon atoms and 6 double bonds: Hexanoic $(C_{6\text{-}0})$; Octanoic $(C_{8\text{-}0})$; Decanoic $(C_{10\text{-}0})$; Dodecanoic $(C_{12\text{-}0})$; 9-Dodecenoic (CIS) $(C_{12\text{-}1})$; Tetradecanoic $(C_{14\text{-}0})$; 9-Tetradecenoic (CIS) $(C_{14\text{-}1})$; Hexadecanoic (CIS) $(C_{16\text{-}0})$; 9-Hexadecenoic (CIS) $(C_{16\text{-}1})$; Octadecanoic $(C_{18\text{-}0})$; 9-Octadecenoic (CIS) $(C_{18\text{-}1})$; 9-Octadecenoic, 12-Hydroxy-(CIS) $(C_{18\text{-}2})$; 9, 12-Octadecadienoic (CIS, CIS) $(C_{18\text{-}2})$; 9, 12, 15 Octadectrienoic (CIS, CIS, CIS) $(C_{18\text{-}3})$; 9, 11, 13 Octadecatrienoic (CIS, TRANS, TRANS) $(C_{18\text{-}3})$; 9, 11, 13 Octadecatrienoic, 4-Oxo (CIS, TRANS,;TRANS) $(C_{18\text{-}3})$; Octadecatetrenoic $(C_{18\text{-}4})$; Eicosanoic $(C_{20})$; 11-Eicosenoic (CIS) $(C_{20\text{-}1})$; Eicosadienoic $(C_{20\text{-}2})$; Eicosatrienoic $(C_{20\text{-}3})$; 5, 8, 11, 14 Eicosatetraenoic $(C_{20\text{-}4})$; Eicosapentaenoic $(C_{20\text{-}5})$; Docosanoic $(C_{22})$; 13 Docosenoic (CIS) $(C_{22\text{-}1})$; Docosatetraenoic (C22-4); 4, 8, 12, 15, 19 Docosapentaenoic (C22-5); Docosahexaenoic $(C_{22\text{-}6})$; Tetracosenoic $(C_{24\text{-}1})$; and 4, 8, 12, 15, 18, 21 Tetracosahexaenoic $(C_{24\text{-}6})$.

Examples of particularly useful diesters of formula II include the unsaturated diester formed by the reaction of sebacic acid with oleyl alcohol:

Useful cyclic diesters falling within formula III include dimerate ester structures formed by the reaction of a $C_{36}$ dimer acid derived from tall oil fatty acids and $C_3$–$C_{24}$, preferably $C_3$–$C_{18}$, more preferably $C_6$–$C_{18}$ alcohol, straight chain or branched, that are unsaturated, containing 1 to 3 carbon-to-carbon double bonds. Examples of such cyclic esters include the following structures, wherein the dimer acid corresponding to structure A is formed by self reaction of linoleic acid, the dimer acid corresponding to structure B is formed by reacting linoleic acid with oleic acid, and the dimer acid corresponding to structure C is formed by reacting linoleic acid with linolenic acid:

wherein each R, same or different, in formulas (A), (B), and (C) is a $C_3$–$C_{24}$ radical, preferably $C_3$–$C_{18}$, more preferably $C_6$–$C_{18}$, straight chain or branched, saturated or unsaturated containing 1 to 3 carbon-to-carbon double bonds. In formula B, at least one R has at least one carbon-to-carbon double bond. Another example of an unsaturated diester (dimerate ester) is an unsaturated diester formed by the reaction of a predominantly $C_{36}$ dimer acid reacted with 2-ethylhexyl alcohol. An additional unsaturated diester (dimerate ester) is formed by the reaction of a predominantly $C_{36}$ dimer acid with tridecyl alcohol.

A representative example of the triester (trimerate ester) of formula IV is the following structure (D);

wherein each $R^1$, $R^2$, and $R^3$, same or different, is a $C_3$–$C_{24}$ radical, preferably $C_3$–$C_{18}$, more preferably $C_6$–$C_{18}$, straight chain, or branched, saturated or unsaturated containing 1 to 3 carbon-to-carbon double bonds.

A particularly useful blend of long chain esters is formed from blends of mono, dimer, and trimer acids, for example, products having CAS#: 61788-89-4. Esters prepared from such products are blends including, primarily, the above $C_{36}$ and $C_{54}$ dimerate and trimerate esters (A), (B), (C) and (D), shown in the above structures, that is predominantly (more than 50% by weight) the $C_{36}$ dimerate esters (A), (B) and (C).

Commercially available blends of useful polybasic acids that can be reacted with $C_3$–$C_{24}$, preferably $C_3$–$C_{18}$, more preferably $C_6$–$C_{18}$ alcohols, straight chain or branched, saturated or unsaturated containing 1 to 3 carbon-to-carbon double bonds to produce the dimerate and trimerate esters, as blends, include the following: EMPOL® 1010 Dimer Acid; EMPOL® 1014 Dimer Acid; EMPOL® 1016 Dimer Acid; EMPOL® 1018 Dimer Acid; EMPOL® 1022 Dimer Acid; EMPOL® 1024 Dimer Acid; EMPOL® 1040 Trimer Acid; EMPOL® 1041 Trimer Acid; EMPOL® 1052 Polybasic Acid; and similar PRIPOL™ products from Uniqema as well as UNIDYME® products from Arizona Chemical.

Particularly useful unsaturated fatty acid esters are made by reacting any of the long chain mono, dimer and/or trimer acids with one or more straight chain or branched $C_3$–$C_{24}$, preferably $C_3$–$C_{18}$, more preferably $C_6$–$C_{18}$ alcohols to produce the esters of formulas I, II, III and IV. In addition, any of the above fatty acids can be reacted with polyhydric compounds, e.g., propylene glycol or ethylene glycol, to produce unsaturated bis-alkyl esters that can be epoxidized, as described herein, to produce bis-alkyl fatty acid esters having increased oxirane ring contents. The above dimer, trimer, and polybasic acids are produced by dimerizing, trimerizing, and polymerizing (oligomerizing) long chain carboxylic acids from the above-mentioned fatty acids. The fatty acids may be mixtures. Accordingly, the dimer acid produced by dimerizing a $C_{18}$ carboxylic acid (typically, a mixture of stearic, oleic, linoleic, and linolenic), after esterification, will result in a blend of numerous dimerate and trimerate esters in accordance with formulas III and IV, including unsaturated esters (i.e., the long chain esters may contain hydrocarbon chains having 1 to 6, generally 1 to 3, carbon-to-carbon double bonds). Any one, or any blend, of the esters of formulas I, II, III and/or IV can be epoxidized, forming an oxirane ring across any or all of the carbon-to-carbon double bonds in accordance with the processes described herein.

Organic hydroperoxides useful in accordance with one embodiment of the thin-film epoxidation method described herein, including catalysts and hydroperoxide solvents that were used in the prior art, and are useful herein, are shown in Table 2.

TABLE 2

HYDROPEROXIDES

| Hydroperoxide | Catalyst (wt % of hydroperoxide) | Conditions |
|---|---|---|
| Hydrogen Peroxide | (10) $MoO_3$ | 10 hr at 50° C. in dioxane |
| t-Butyl hydroperoxide | (12) $MoO_3$ | 8 hr at 80° C. in dioxane |
| 2-Cyclohexenyl hydroperoxide | (2) $MoO_2$ $acac_2$* | 1 hr at 70° C. |

TABLE 2-continued

HYDROPEROXIDES

| Hydroperoxide | Catalyst (wt % of hydroperoxide) | Conditions |
|---|---|---|
| Cumyl hydroperoxide | (0.03) V naphthenate | 1 hr at 90° C. in ethylbenzene |
| 5-Butyl hydroperoxide | (1) Voctoate | 6 hr at 46° C. |
| t-Butyl hydroperoxide | (8) Molybdates** | 2 hr at 135° C. in ethylacetate |
| Cumyl hydroperoxide | (19) MoO$_3$ | 6 hr at 100° C. in cumene |
| t-Amyl hydroperoxide | (2) Mo naphthenate | 2 hr at 130° C. |
| Cumyl hydroperoxide | (1.5) Molybdates | 0.75 hr at 110° C. |
| 2,4-Dimethyl-3-keto-2-pentyl hydroperoxide | (3) Molybdates | 1 hr at 85° C. in methanol |
|  | (1.5) Molybdates | 1 hr at 75° C. in methanol |
| 1-Tetralin hydroperoxide | (3.5) Molybdates | 1 hr at 85° C. chloroform |

*Acetylacetenoate
**Equal weights of Na$_2$ MoO$_4$ and Na$_4$ (PMo$_{12}$O$_{40}$)

Surprisingly, the original hydroperoxides will react with the double bond(s) contained in the unsaturated substrates without the metal catalysts when reacted in a thin-film, as described herein. The inclusion of the above-mentioned catalysts, however, may improve yields.

Figure 2A:
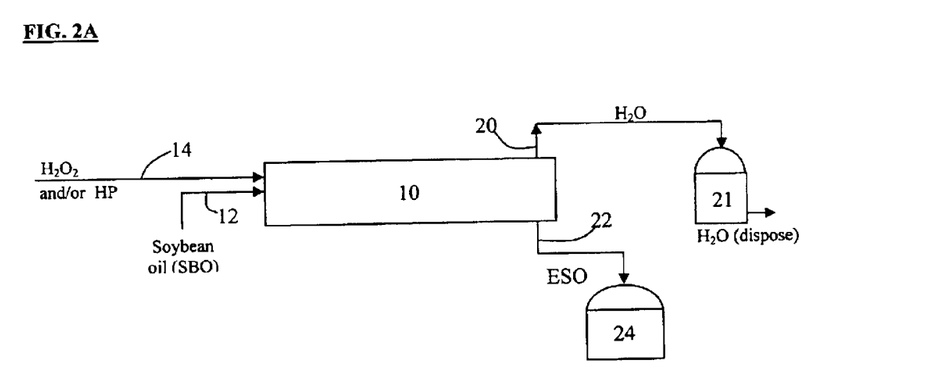
FIGS. 2A and 2B are schematic flow diagrams of two preferred embodiments of processes, as described herein, for epoxidizing an unsaturated substrate, such as soybean oil or an alkyl fatty acid ester, by oxidation of the unsaturated substrate directly with hydrogen peroxide in the thin-film reactor.
Figure 2B:
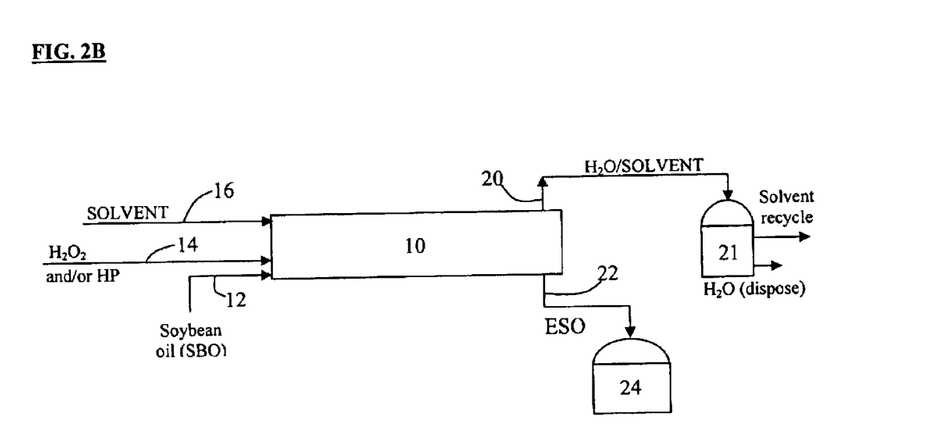

In accordance with the flow diagram shown in FIG. 2, an unsaturated substrate, e.g., an alkyl fatty acid ester or an unsaturated vegetable oil, is fed to a thin-film reactor 10, e.g., a ROTOTHERM® thin-film processor, or spinning disc reactor, or wiped film evaporator, or a thin-film evaporator, through feed conduit 12 and simultaneously, a hydrogen peroxide and/or an organic hydroperoxide reactant is fed to the thin-film reactor 10 through feed conduit 14. Preferably, both reactants are combined and homogenized prior to being added to the thin-film reactor 10 in a reactant mixture through a single feed conduit, e.g., 12. The thin-film reactor 10 is maintained at a temperature in the range of about 65° F. to about 150° F., preferably in the range of about 100° F. to about 130° F., and at a pressure of about 25 to about 400 mm Hg absolute.

Water contained in the reactants and reaction water is evaporated during processing and is removed from the thin-film reactor 10 through overhead conduit 20 and collected in water collection vessel 21. The epoxidized product, e.g., epoxidized soybean oil (ESO), is removed from a bottoms product discharge conduit 22 for collection in product collection vessel 24.

Figure 3A:
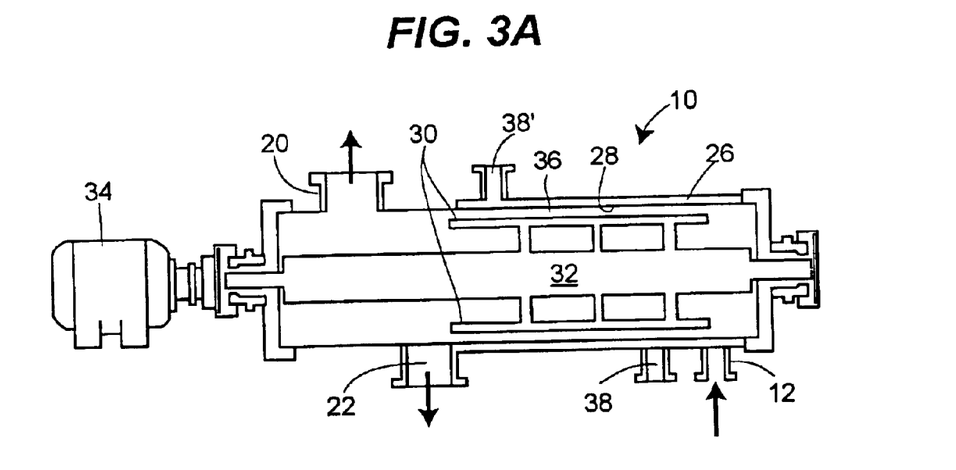
FIGS. 3A and 3B are cross-sectional views of a typical thin-film reactor, showing co-current flow of reactants (FIG. 3A) and counter-current flow of reactants (FIG. 3B).
Figure 3B:
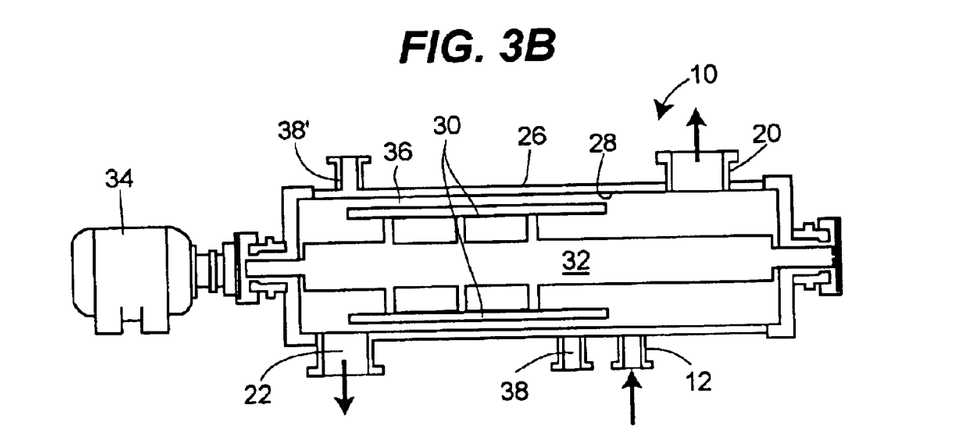

A typical thin-film reactor 10, best shown in FIGS. 3A and 3B, includes a horizontally disposed cylindrical casing 26, preferably formed from stainless steel, nickel, INCONEL®, MONEL®, HASTELLOY®, or titanium, having a smooth inner process wall 28 on which the reactants form a thin-film as a result of centrifugal force exerted by rotor blades 30. The rotor blades 30 are connected to a horizontal shaft 32 rotated by motor 34. Inner process wall 28 is heated to a temperature in the range of about 65° F. to about 150° F., preferably about 100°F. to about 130°F. to initiate the epoxidation reaction. The smooth inner process wall 28 is heated by circulating a heating medium 36, e.g., THERMINOL®, through a cylindrical passageway disposed adjacent to a portion of the inner process wall 28 that is adjacent to the rotor blades 30. The heating medium 36 is fed to the reactor 10 through heating medium conduit 38, and the heating medium 36 recirculates through conduit 38' to heat the reactants to the desired reaction temperature. Once the reaction begins, it is very exothermic. The inner process wall 28 then is cooled to maintain the desired reaction temperature by circulating a cooling medium, e.g., cooling tower water, through a cylindrical passageway disposed adjacent to a portion of the inner process wall 28 that is adjacent to the rotor blades 30. While FIGS. 3A and 3B show a single heating or cooling medium 36 circulating through the cylindrical passageway, it is understood that two non-interconnected passageways can be included (not shown)—one for a heating medium to bring the temperature of the reactants up to reaction temperature and a separate passageway for cooling medium to maintain isothermal conditions within the thin-film reactor. Upon reaching reaction temperature, circulation of heating medium would be ceased and circulation of cooling medium would begin. As described earlier, the epoxidation reaction forms an oxirane ring at one or more double bonds contained in the unsaturated substrate reactant entering the thin-film reactor 10 through feed conduit 12.

The rotor blades 30 provide a turbulent thin-film in contact with the heated, smooth inner process wall 28. The thin-film of unsaturated substrate and H$_2$O$_2$ reactants are in contact with process wall 28 at all times, regardless of the feed rate of reactants and evaporation rate of water. This thin-film of reactants is constantly renewed as the progressively more concentrated material is displaced towards the bottoms product discharge conduit 22 by the incoming reactants. High vacuum, e.g., 25 to 400 mm Hg absolute, is maintained in the system to minimize the processing temperature, enhance water removal and increase the rate of reaction. As the residence time is generally measured in seconds, the degradation of heat sensitive materials is minimized.

The preferred molar ratios of reactants are about 0.5–1.0 to about 1.0–0.05, more preferably about 0.9–1.0 to about 1.0–0.5, and most preferably from about 1.1–1.0 to about 1.0–0.9, especially about 1:1, unsaturated substrate to peroxide. Lower amounts of peroxide can provide for desired amounts of unsaturation in the epoxidized product. The feed rates of the reactants are dependent on the desired epoxidized product volume. The feed rates of the reactants can also be varied to assist in controlling the reaction at the desired temperature or product quality.

In accordance with another embodiment, as shown in FIG. 1B, one or more organic solvents, such as heptane or octane and/or aromatic solvents, such as toluene is added to the reactants, e.g., through feed conduit 16, preferably mixed with and homogenized with other reactants to form a single reactant mixture fed to the thin-film reactor through feed conduit 12, for better contact and reaction of the hydrogen peroxide with the unsaturated substrate.

We claim:

1. A method of epoxidizing an unsaturated compound having a carbon-to-carbon double bond to form an oxirane ring across the double bond comprising
    adding to said unsaturated compound an oxidizing agent selected from hydrogen peroxide, acetaldehyde monoperacetate, an organic hydroperoxide, or a combination thereof, to form a reactant mixture; and
    forming the reactant mixture in a film against a wall of the thin-film reactor that is at a temperature sufficient for reaction of the oxidizing agent with the unsaturated compound to form an oxirane ring across a double bond of the unsaturated compound.

2. A method in accordance with claim 1, wherein the method is a continuous method such that the reactant mixture is continuously fed to the thin-film reactor and the epoxidized unsaturated compound is continuously recovered from the thin-film reactor, maintained under isothermal conditions.

3. A method in accordance with claim 2, further including the step of evaporating water from the thin-film reactor.

4. A method in accordance with claim 1, wherein the film of reactants is heated to a temperature in the range of about 65° F. to about 150° F.

5. A method in accordance with claim 1, wherein the molar ratio of unsaturated compound to the oxidizing agent is in the range of 0.5–1.0 to 1.0–0.05.

6. A method in accordance with claim 2, further including the step of continuously forcing a film of said reactant mixture against said heated or cooled reactor wall, by centrifugal force, for efficient heating or cooling, in film form, of the reactant mixture.

7. A method in accordance with claim 2, further including the additional step of recycling non-epoxidized and/or incompletely oxidized unsaturated compound to the thin-film reactor for epoxidation of non-oxidized and/or incompletely epoxidized unsaturated compound.

8. A method in accordance with claim 1, wherein the feed rates of unsaturated compound, and peroxide can be varied to affect production rates and product quality.

9. A method in accordance with claim 8, wherein variable feed rates allow for changes in production rates and product quality.

10. A method in accordance with claim 5, wherein the molar ratio of unsaturated compound to oxidizing agent is in the range of about 0.9–1.0 to about 1.0–0.5.

11. A method in accordance with claim 5, wherein the molar ratio of unsaturated compound to oxidizing agent is in the range of about 1.1–1.0 to about 1.0–0.9.

12. A method in accordance with claim 5, wherein the molar ratio of unsaturated compound to oxidizing agent is about 1:1.

\* \* \* \* \*